US008326548B2

(12) United States Patent
Oh (10) Patent No.: US 8,326,548 B2
(45) Date of Patent: Dec. 4, 2012

(54) PREDICTION OF WAX APPEARANCE TEMPERATURE AND SOLID WAX AMOUNT BY REDUCED SPECTRAL ANALYSIS USING FTIR SPECTROSCOPY

(75) Inventor: Kyeongseok Oh Oh, Salt Lake City, UT (US)

(73) Assignee: Kyeongseok Oh, Salt Lake City, UT (US)

( * ) Notice: Subject to any disclaimer, the term of this patent is extended or adjusted under 35 U.S.C. 154(b) by 300 days.

(21) Appl. No.: 12/785,441

(22) Filed: May 22, 2010

(65) Prior Publication Data

US 2011/0288788 A1 Nov. 24, 2011

(51) Int. Cl.
*G01N 33/28* (2006.01)
*G01N 33/26* (2006.01)
(52) U.S. Cl. ..................... 702/25; 250/339.06

(58) Field of Classification Search ............. 702/25, 702/30; 250/339.06, 339.07
See application file for complete search history.

(56) References Cited

U.S. PATENT DOCUMENTS 6,035,706 A * 3/2000 Campagnolo et al. ....... 73/64.42
6,841,779 B1 * 1/2005 Roehner et al. .......... 250/339.07

\* cited by examiner

*Primary Examiner* — Bryan Bui (57) ABSTRACT

A method that uses corrected areas integrated at two different wavelength ranges, 1402-1324 $cm^{-1}$ and 735-715 $cm^{-1}$. The invention uses the reduced form of FTIR spectral integration. The invention provides reliable data in the variety of applications regardless of FTIR spectral instability occurring unexpectedly, such as loading sample thickness, sample cell location changes of FTIR light source passes, volume changes during cooling procedure, existence of emulsified water, moisture building on the surface of FTIR crystals.

17 Claims, 6 Drawing Sheets

PREDICTION OF WAX APPEARANCE TEMPERATURE AND SOLID WAX AMOUNT BY REDUCED SPECTRAL ANALYSIS USING FTIR SPECTROSCOPY

BACKGROUND OF THE INVENTION

High molecular weight paraffinic waxes in a crude oil or in a gas condensate start to precipitate when the temperature, a major parameter, decreases below the wax appearance temperature (WAT). WAT is defined the onset temperature that the solid phase wax particles start to precipitate from the continuous liquid phase. Other terms, such as cloud point, wax precipitation temperature and wax appearance point are all interchangeable. There have been various techniques used in determining the WAT values. In the case that the testing oils are transparent, ASTM D2500 can be often used to determine the WAT. Previous studies have presented the difference in WAT data when determined by three different measurement methods—microscopy, viscosity and differential scanning calorimetry. The result showed that highest WAT values were dominantly observed from microscopic measurement. The comparison of WAT values and the detection limits with various procedures is well known in the art. It should be noted that WAT is dependent upon the cooling rate and shear history. The faster cooling during pipeline transport occurs when the temperature gradient between the pipe inside and outside is significantly increased. The faster cooling condition accelerates the wax formation resulting in the higher WAT value. High mechanical shear or high flow rate, suppresses the wax formation in isothermal condition.

The pour point is another important characteristic temperature that is usually determined by ASTM D97. Flow discontinuity can occur by either wax deposition or wax gel formation. While the wax deposition can be initiated during flow, wax gel formation occurs under static conditions caused by shutdown. Subsequent to shutdown, if the wax gel develops, certain level of upstream pressure is necessary to overcome the yield stress of the gel along the pipeline for restart. Approximately two percent of precipitated wax is needed to prevent the oil flow during pour point measurement. In the static condition, the yield stress of gelled oils becomes greater during cooling, at temperatures below the pour point. Generated solid waxes in cooling environments continuously contribute to the increase of gel strength.

It is possible that oils from different origins have a same WAT value even though they contain different wax amounts and constituents. Three examples of oils in terms of the WAT data and wax constituents are listed below.

Oil with the lower WAT but faster increase of precipitated wax amount—Supposed that the WAT values of OIL-1 and OIL-2 are T1 and T2 (T1>T2), however OIL-2 shows the faster increase of wax amount during cooling. The faster increase of the precipitated wax amount in OIL-2 could be attributed to the higher contents of total wax than the total wax in OIL-1. In addition, the wax compositions are different in OIL-1 and OIL-2. Since it is well known in the art that the higher molecular weight waxes come out in an early stage from the oil phase, OIL-1 may have more wax amounts of the higher molecular weight waxes than OIL-2, however OIL-2 has more total wax content than OIL-1.

Oils with same WAT values-If there are two different oils with the same composition except with a difference in total wax compositions, the oil containing waxes of higher carbon number distribution may contain less overall wax amount than the oil containing waxes of lower carbon number distribution.

Oils with different WAT values-Oil containing more waxes can have a higher WAT as long as a wax molecular distribution is similar. More waxes of higher molecular weights also results in higher WAT.

U.S. Pat. No. 6,841,779 shows how to determine the WAT and solid wax amount versus temperature using FTIR and differential scanning calorimetry. U.S. Pat. No. 6,841,779 has several disadvantages because of its reliance on a single peak to predict the solid wax amount. The reliance on a single peak makes the solid wax amount determination less accurate because a single peak is affected by changes in the sample.

The current invention overcomes the limited access of Fourier Transform Infrared (FTIR) spectra to predict a WAT as well as a solid wax amount precipitated at temperatures below the WAT by using the reduced form derived from two peaks in the FTIR. The reduced form is not affected by variations in the sample allowing for consistent WAT determination as well as prediction of solid wax amount. This invention has the following advantages over the prior art.

The baseline shift due to variances in sample thickness does not affect the value of the reduced form in this spectral analysis The analysis is not affected where light passes through the sample.

The analysis is not affected by sample volume.

The analysis is not affected by moisture generation on the outer surfaces of FTIR crystal windows (NaCl) during cooling process.

The analysis is not affected by a baseline shift up due to water in the oil sample The analysis is not affected by the degree of transparency of NaCl crystal. (the NaCl crystals do not have to be transparent)

It is important to know when and how much wax is precipitated in cooling environments where there are existing wax problems. This invention shows the enhanced applicability of FTIR spectra to determine the WAT as well as the amount of precipitated wax in temperature variance.

Analytic Background

Spectroscopic analysis follows the Beer-Lambert law shown below. There is a linear relation between a spectral absorbance and a concentration of an interest material.

$$A = -\log T = a \cdot b \cdot c \quad \text{(Eq. 1)}$$

Figure 1:
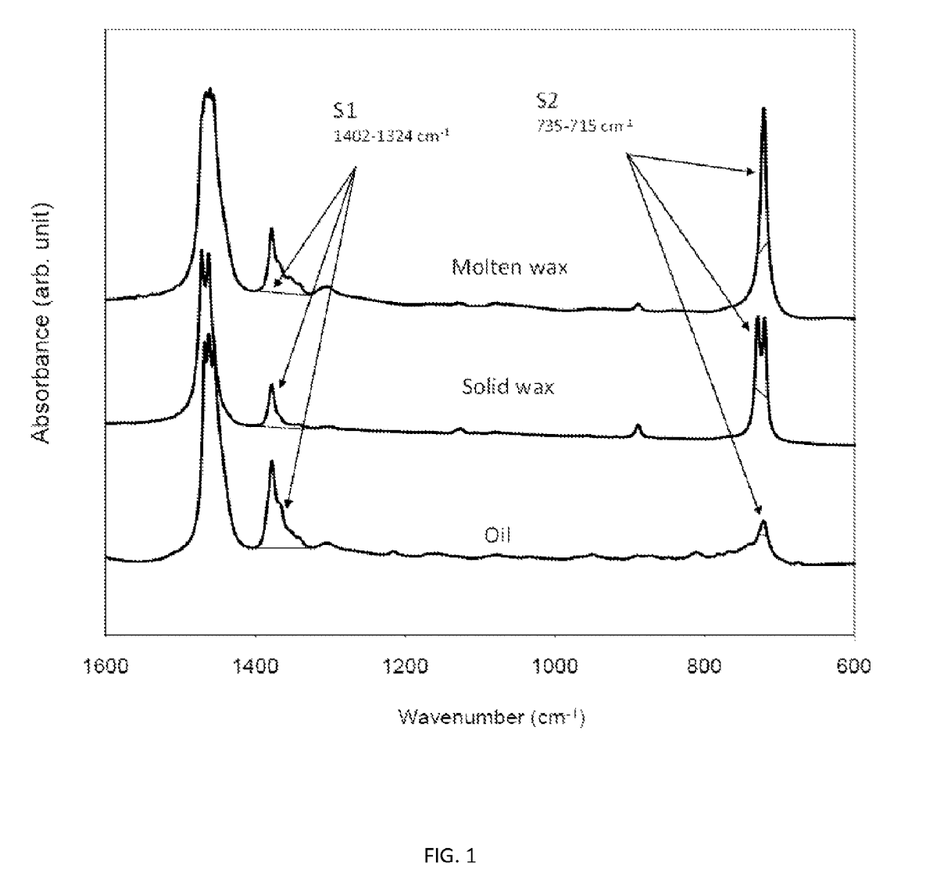
FIG. 1 is the FTIR spectra of molten wax, solid wax, and a crude oil.

A: absorbance
T: transmittance
a: absorptivity
b: pathlength
c: concentration of the material that absorbs the light source FIG. 1 shows the FTIR spectral absorbance of the paraffin wax in molten state, in solid state, and an oil example at wavelength range of 1600-600 cm$^{-1}$. The interest in wax analysis is in two regions, one is at 1402-1324 cm$^{-1}$ and the other is at 735-715 cm$^{-1}$. The spectral responses of these regions are well known in the art. This invention uses both wavelength regions. It should be noted that the corrected area represents the spectral integrated area subtracted the base from the total area at a designated wavelength region.

S1: corrected area at wave number range of 1402-1324 cm$^{-1}$ (CH2 vibration)

S2: corrected area at wave number range of 735-715 cm$^{-1}$ (CH2 rocking, significant changes in case of solid wax generation)

Supposed the resolution of FTIR is 1 cm$^{-1}$.

$$S1 = \sum_{j=1324}^{1402} A_j = (K_{11}C_1 + K_{12}C_2) \cdot l \quad \text{(Eq. 2)}$$

$$S2 = \sum_{j=715}^{735} A_j = (K_{21}C_1 + K_{22}C_2) \cdot l \quad \text{(Eq. 3)}$$

Both S1 and S2 were the spectral response obtained from the contribution of the liquid phase including dissolved wax and the solid phase of wax.

In (Eq. 2) and (Eq.3),
Aj: absorbance at wavelength j
l: pathlength
K: contribution factor
here, K values are classified into $$K_{11} = k_{1,1324} + k_{1,1325} + k_{1,1326} + \ldots + l_{1,1402} \quad \text{(Eq.4)}$$

$$K_{12} = k_{2,1324} + k_{2,1325} + k_{2,1326} + \ldots + k_{2,1402} \quad \text{(Eq.5)}$$

$$K_{21} = k_{1,715} + k_{1,716} + k_{1,717} + \ldots + k_{1,735} \quad \text{(Eq.6)}$$

$$K_{22} = k_{2,715} + k_{2,716} + k_{2,717} + \ldots + k_{2,735} \quad \text{(Eq.7)}$$

$K_{11}$: Contribution factor from the solid wax at the wavelength region of 1402-1324 cm$^{-1}$
$K_{12}$: Contribution factor from the liquid phase including dissolved wax at the wavelength region of 1402-1324 cm$^{-1}$
$K_{21}$: Contribution factor from the solid wax at the wavelength region of 735-715 cm$^{-1}$
$K_{22}$: Contribution factor from the liquid phase including dissolved wax at the wavelength region of 735-715 cm$^{-1}$
$C_1$: Concentration of solid wax
$C_2$: Concentration of liquid phase including dissolved wax For example, $k_{1,1324}$ represents the FTIR contribution factor of solid wax at the wavelength of 1324 cm$^{-1}$, and $k_{2,735}$ represents the FTIR contribution factor of liquid phase including dissolved wax at the wavelength of 735 cm$^{-1}$.

By rearranging the concentration of solid wax in (Eq.2) and (Eq.3), $$S1 = \sum_{j=1324}^{1402} A_j = (K_{11}x + K_{12}(1-x)) \cdot l' \quad \text{(Eq. 8)}$$

$$S2 = \sum_{j=715}^{735} A_j = (K_{21}x + K_{22}(1-x)) \cdot l' \quad \text{(Eq. 9)}$$

Here, x and (1−x) represent the weight fraction of solid (precipitated) wax and the weight fraction of liquid phase including dissolved wax, respectively. And l' represents the constant containing the combined contribution of pathlength and unit conversion factor when the concentration (C) in the equations (6), (7) convert to fraction (x).

As a liquid sample starts to generate the solid wax, the total volume decreases. The location FTIR light source passes is often changed during the measurement. In the case that a large number of solid wax generates, the FTIR absorbance shifts up. However, it is important that the reduced spectra area, S2/S1, does not change. It should be noted that the value change of S2 is smaller when it is compared to the value change of S1 determined at temperatures below the WAT. Solid wax affects the value of S1 in a negligible manner but increases the value of S2. The invention uses S1 as a reference value to S2 value because the sensitivity of S1 is considerably less than that of S2 in the presence of solid wax. The reduced spectral area provides a reliable value regardless of sample volume changes, existence of water, location change where FTIR light source passes. As we can see, the reduced spectral area is presented in (Eq.10).

$$S2|_{Reduced} = \frac{S2}{S1} \quad \text{(Eq. 10)}$$

The reduced spectral area increases in a mildly linear manner with decreasing temperatures. The reduced spectral area data of a mineral oil shows no deviation from the linear increase because the mineral oil does not contain paraffinic waxes (data shown in Table 1).

TABLE 1

FTIR data of S1, S2 and the reduced spectral area (S2/S1) from a mineral oil.

| Temperature (° C.) | S1 | S2 | S2/S1 |
|---|---|---|---|
| 50 | 34.5866 | 1.9841 | 0.057366 |
| 30 | 35.4546 | 2.3717 | 0.066894 |
| 20 | 35.8427 | 2.5914 | 0.072299 |
| 10 | 36.3970 | 2.8832 | 0.079215 |
| 5 | 36.4242 | 2.9752 | 0.081682 |

However, in the case that there are paraffinic waxes in the oil, the reduced spectral area deviates significantly from the linear increase during cooling process at the temperature below the WAT. The value increase of S2 is much greater than the value change of S1. Table 2 and Table 3 present the reduced spectral area of two model oils, the 5 weight percent and the 7 weight percent of wax oils in temperature variance.

TABLE 2

FTIR data of S1, S2 and the reduced spectral area (S2/S1) from 5 weight percent wax model oil.

| Temperature (° C.) | S1 | S2 | S2/S1 |
|---|---|---|---|
| 55 | 30.4310 | 1.9786 | 0.065019 |
| 50 | 30.6614 | 2.0838 | 0.067962 |
| 45 | 30.8562 | 2.1815 | 0.070699 |
| 40 | 30.9677 | 2.2796 | 0.073612 |
| 35 | 31.1643 | 2.3702 | 0.076055 |
| 30 | 31.3825 | 2.4899 | 0.079340 |
| 25 | 31.5047 | 2.8455 | 0.090320 |
| 20 | 31.5694 | 3.2136 | 0.101795 |
| 15 | 31.6507 | 3.6019 | 0.113802 |
| 10 | 31.7255 | 3.9591 | 0.124792 |
| 5 | 31.9356 | 4.2621 | 0.133459 |

TABLE 3

FTIR data of S1, S2 and the reduced spectral area (S2/S1) from 7 weight percent wax model oil.

| Temperature (° C.) | S1 | S2 | S2/S1 |
|---|---|---|---|
| 50 | 39.0337 | 2.6536 | 0.067982 |
| 45 | 39.3371 | 2.7452 | 0.069787 |
| 40 | 39.4782 | 2.8688 | 0.072668 |
| 35 | 39.6414 | 2.9908 | 0.075446 |
| 27 | 39.734 | 3.5820 | 0.090149 |

TABLE 3-continued

FTIR data of S1, S2 and the reduced spectral area (S2/S1) from 7 weight percent wax model oil.

| Temperature (° C.) | S1 | S2 | S2/S1 |
|---|---|---|---|
| 25 | 39.8709 | 3.8416 | 0.096351 |
| 20 | 39.7905 | 4.3464 | 0.109232 |
| 15 | 40.0401 | 4.8105 | 0.120142 |
| 10 | 40.0905 | 5.2796 | 0.131692 |
| 5  | 40.1245 | 5.6202 | 0.140069 |

As the solid waxes generate, the deviation from the mild linear increase of the reduced spectral area became greater with increasing wax amount. The difference between the measured data and the linear extrapolation of reduced spectral area implies the wax amount in the sample.

The difference of the measured data and the linear extrapolation is shown below.

$$S2|_{reduced} - \frac{S2}{S1}\bigg|_{etp} = \frac{S2}{S1} - \frac{S2}{S1}\bigg|_{etp} \quad (Eq. 11)$$

Here, subscript etp represents the extrapolation of linear increase of reduced spectral area (S2/S1).

Since there is no solid wax content in the extrapolation of reduced spectral area, $K_{21}=0$ $$\frac{S2}{S1} - \frac{S2}{S1}\bigg|_{etp} = \frac{K_{21}x + K_{22}(1-x)}{K_{11}x + K_{12}(1-x)} - \frac{K_{22}(1-x)}{K_{11}x + K_{12}(1-x)} \quad (Eq. 12)$$

$$= \frac{K_{21}x}{K_{11}x + K_{12}(1-x)}$$

If the value of denominator is much greater than the value in numerator, the assumption that S1 considers to be a constant can be applicable (less than 5 percent of value changes, refer to Table 2 and Table 3). Therefore $$K_{11}=K_{12}. \quad (Eq. 13)$$

Return to (Eq.12)

$$\frac{S2}{S1} - \frac{S2}{S1}\bigg|_{etp} = \frac{K_{21}x}{K_{12}} = \frac{K_{21}x}{K_{11}} \quad (Eq. 14)$$

There are two different phases in solid wax, orthorhombic and hexagonal phases. The orthorhombic phase of solid wax transits to hexagonal phase during heating program. The left-hand-side of (Eq.14) became 0.9 for orthorhombic phase and 0.85 for hexagonal phase obtained from pure wax (x=1). The precipitated wax does not need to be orthorhombic phase. The constant was chosen to 0.85.

$$\frac{S2}{S1} - \frac{S2}{S1}\bigg|_{etp} = \frac{S2}{S1}\bigg|_{solid} - \frac{S2}{S1}\bigg|_{molten} \cong 0.85 \quad (Eq. 15)$$

That is, $$\frac{K_{21}}{K_{11}} = 0.85$$

(Eq.15) can be represented to $$x = 1.2 \cdot \left(\frac{S2}{S1} - \frac{S2}{S1}\bigg|_{ept}\right) \quad (Eq. 16)$$

SUMMARY OF THE INVENTION

High molecular weight paraffinic waxes start to precipitate when the surrounding temperature drop below the wax appearance temperature (WAT). While the WAT measurements have been widely explored, the precipitated wax amount has been determined by a very expensive process. This expensive process involves extracting wax contents at each temperature set This invention determines the WAT as well as the precipitated wax amount at temperatures below the WAT using FTIR spectroscopy. This invention improves significantly in the data reliability and in the data stability by adapting the reduced form of FTIR spectral area. The reduced form of FTIR spectral area uses two different wavelength regions, one is 1402-1324 cm$^{-1}$ and the other is 735-715 cm$^{-1}$. Reduced spectral area is defined as shown in equation (10).

$$S2_{Reduced} = \frac{S2}{S1} \quad (Eq. 10)$$

Here S1 and S2 represent the corrected areas at the wavelength of 1402-1324 cm$^{-1}$ and 735-715 cm$^{-1}$, respectively. S1 plays a reference value to S2 to adjust the possible fluctuation of FTIR spectra. The instability occurs in various cases, such as the change of sample thickness, baseline shift by water content, moisture built on the outer surface of FTIR crystals, and location change of FTIR light source passes. The WAT is determined by the deviation onset from the mild linear increase of reduced spectral area during the cooling process. The invention also provides the precipitated wax amount at temperatures below the WAT. This invention can also used to determine the WAT in diverse origin of oil sources.

Embodiments of a method are also described. In one embodiment, the method is a method for determining material properties comprising a first process that comprises, performing a reduced spectral analysis on the material and producing a first wavelength range at a temperature. Then determining a first area for a second wavelength range and determining a second area for a third wavelength range. Then calculating the reduction from of the first area and the second area. The method includes a second process comprising repeating the first process at least three times using the same material at a different temperature for each repetition. Then creating a graph showing the ratios versus the temperatures and determining a slope change in the graph. Other embodiments of the method are also described.

Other aspects and advantages of embodiments of the present invention will become apparent from the following detailed description, taken in conjunction with the accompanying drawings, illustrated by way of example of the principles of the invention.

LIST OF REFERENCES

1) Annual Book of ASTM-Standards, "Petroleum Products, Lubrications. West Conshohocken, Pa.: American Society for Testing and Materials," Sect. 5., 1999.
2) Pedersen, K. S.; Skovborg, P.; Rønningsen, H. P. "Wax Precipitation from North Sea Crude Oils. 4. Thermodynamic Modeling," Energy Fuels 1991, 5, 924-932.
3) Coutinho, J. A. P.; Daridon, J.-L. "The Limitations of the Cloud Point Measurement Techniques and the Influence of the Oil Comparison on Its Dectection," Pet. Sci. Tech. 2005, 23, 1113-1128.
4) Oh, K.; Deo, M. D. "Characteristics of wax gel formation in the presence of asphaltenes," Energy Fuels 2009, 23(3), 1289-1293.
5) Zerbi, G.; Magni, R.; Gussoni, M.; Moritz, K. H.; Bigotto, A.; Dirlikov, S. Molecular mechanics for phase transition and melting of n-alkanes: A Spectroscopic study of molecular mobility of solid n-nonadecane, J. Chem Phys, 75(7), 1981, pp 3176-3194.
6) Snyder, R. G.; Maroncelli, M.; Strauss, H. L.; Hallmark, V. M. Temperature and phase behavior of infrared intensities: The poly(methylene) chain, J. Phys. Chem. 1986, 90, pp 5623-5630.
7) Coutinho, J. A. P.; Ruffier-Méeray, V. Experimental Measurements and Thermodynamic Modeling of Paraffinic Wax Formation in Undercooled Solutions, Ind. Eng. Chem. Res. 1997, 36, pp 4977-4983.
8) Oh, K.; Jemmett, M.; Deo, M. D. "Yield Behavior of Gelled Waxy Oil: Effect of Stress Application in Creep Ranges," Ind. Eng. Chem. Res. 2009, 48, 8950-8953.
9) Oh, K.; Gandhi, K.; Magda, J. J.; Deo, M. D. "Yield stress of waxy gel using vane method" Pet. Sci. Tech. 2009, 27, 2063-2073.

DETAILED DESCRIPTION

Oils used for one embodiment were formulated model oils, water-in-oil emulsified oils and a crude oil. Even though this process has been applied to model oils, many different oil types and material could be used. Additionally, other procedures could be used to collect the data shown. The formulated model oils were prepared by mixing of mineral white oil and a well-defined solid wax. The carbon number distribution of wax for one embodiment is between C21-C38. For this embodiment, two different weight percents of wax content were used (5 weight percent and 7 weight percent). Emulsified oils were prepared by a mineral white oil, solid wax, hydrophobic surfactant and water. Water contents were shown in weight percents. Table 4 shows the components of water-in-oil emulsified oils. In order to ensure the emulsion formation up to 30 weight percent of water, larger amount of surfactant was used. A crude oil with known amount of wax contents was also used.

TABLE 4

Compositions of water-free model oil and 10 percent and 30 percent emulsions

| | | Oil Phase | | | Volume | Pour |
|---|---|---|---|---|---|---|
| Emulsion | Water (wt. %) | Mineral oil (wt %) | Wax (wt. %) | Span 80 (wt %) | fraction of water | Point (° C.) |
| Anhydrous | 0 | 87 | 3 | 10 | 0 | 14 |
| 10% water | 10 | 78.3 | 2.7 | 9 | 0.09 | 13 |
| 30% water | 30 | 61.11 | 1.89 | 7 | 0.27 | 13 |

The sealed liquid cell equipped with temperature control was used to measure the FTIR spectra. A liquid sample at 60° C. was charged into the heated liquid cell with the sample thickness (pathlength) of 0.1 mm. Sample spacer of 0.1 mm-thick was installed in the sandwich type of NaCl crystals with a diameter of 3 mm. A well-controlled water bath was used to maintain each set temperature of a liquid sample. FTIR spectra were collected after the temperature was stabilized for 30 minutes at each temperature set. The corrected area was calculated by the built-in software in the PerkinElmer FTIR spectroscopy.

Figure 2:
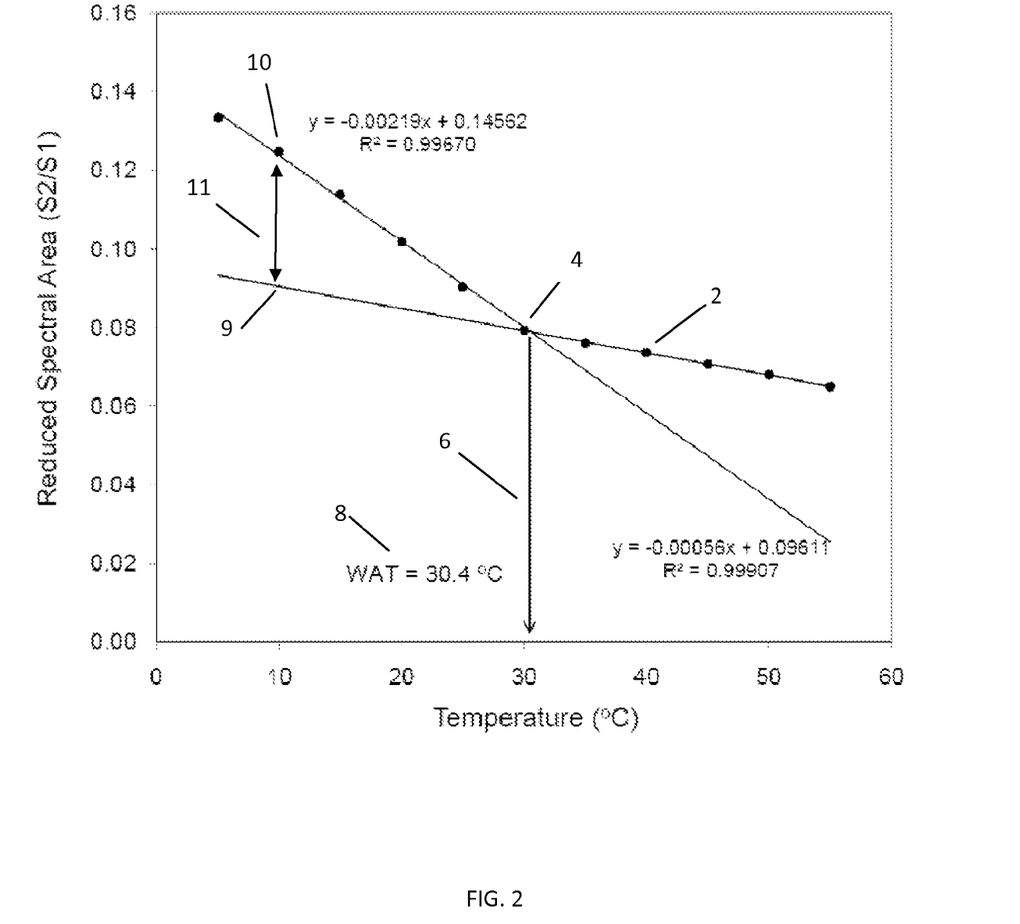
FIG. 2 is the reduced spectral area versus temperature measured with 5 weight percent wax oil.

FIG. 2 is the reduced spectral area versus temperature measured with 5 weight percent wax oil. In one embodiment data points 2 are equal to the reduction of a first area and a second area of a spectral analysis of oil at different temperatures. Slope break point 4 shows were the data points 2 linear plot changes slope based on changes in temperature. Line 6 shows the temperature that is associated with the change in slope. For one embodiment line 6 shows the wax appearance temperature for an oil. Horizontal axis value 8 is the horizontal axis value corresponding to the slope break 4. In one embodiment horizontal axis value 8 is the wax appearance temperature for an oil.

In addition to determining the WAT, FIG. 2 can be used to determine the wax amount in the oil for a given temperature. First data point 9 and second data point 10 or related because they are located on the same vertical axis. Difference 11 is the difference between data point 9 and data point 10. This difference can be multiplied by a constant to determine the percent of wax amount in the oil at the temperature intersecting the vertical axis defined by data point 9 and data point 10. The constant can be determined as shown in equations 15 and 16.

For one embodiment of the invention, FIG. 2 shows how the WAT is determined. The measurement starts from a temperature high enough to ensure no pre-existing solid waxes. As shown in Table 1, 2, and 3, individual FTIR spectra measured at each set temperature were opened and software was used to calculate the corrected areas in both wavelength ranges, 1402-1324 $cm^{-1}$ and 735-715 $cm^{-1}$. The corrected area at 1402-1324 $cm^{-1}$ defined to S1 and the corrected area at 735-715 $cm^{-1}$ to S2, respectively. The reduced spectral area is defined to S2/S1 at each set temperature. FIG. 2 shows the reduced spectral areas of 5 weight percent wax oil in temperature variance. The data were measured at individual set temperature by cooling process. The mild linear increase with decreasing temperatures was observed at temperatures above the WAT, which accounts that the solid wax dissolves in the oil phase. The deviation onset from the mild linear increase is determined as the WAT. The value of deviation onset was obtained by identifying the intersection between two linear lines, one is mild linear line chosen to plot at temperatures higher than the WAT and the other with steeper slope chosen to plot at temperatures below the WAT.

The difference between the measured value of reduced spectral area and the extrapolated value of reduced spectral area implies the amount of solid wax. The factor, 1.2 is used to count the amount of precipitated wax in individual set temperatures.

Figure 3:
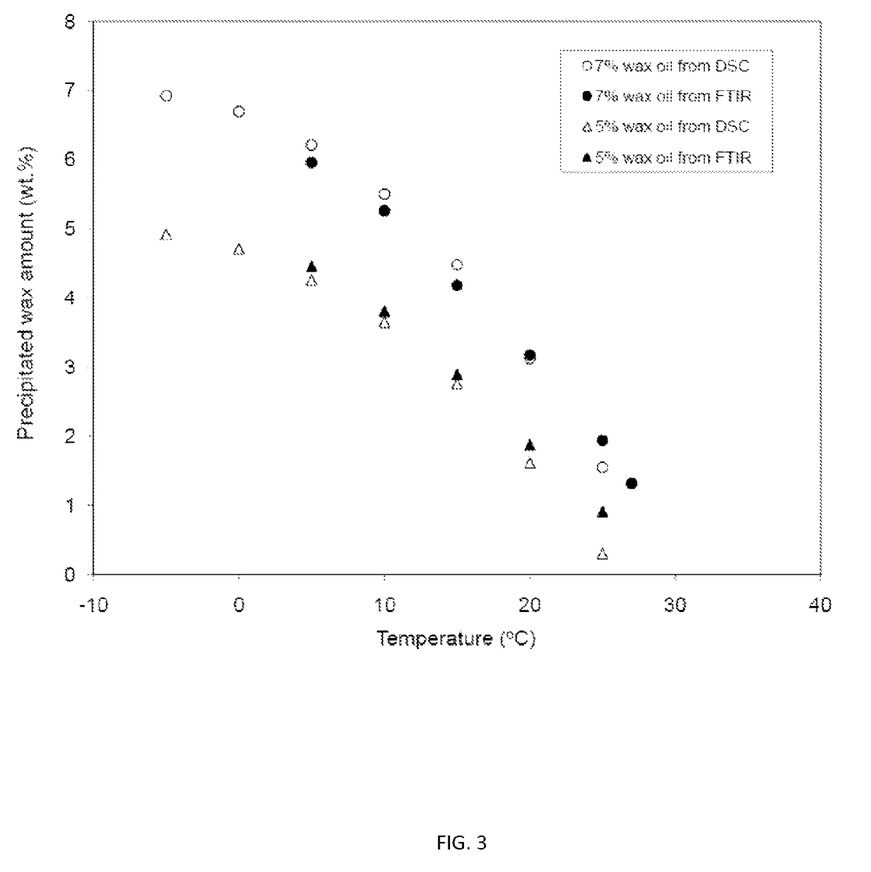
FIG. 3 is the precipitated wax amount with respect to the temperatures. Differential scanning calorimetry data also represented for comparison. The data were obtained with 5 weight percent and 7 weight percent wax oils.

FIG. 3 shows the wax amount versus temperatures with 5 weight percent and 7 weight percent wax oils. The amount calculated from the DSC method was also shown as comparison. The DSC cell containing oil sample was initially cooled down to −20° C. for 10 minutes to precipitate the total waxes dissolved in 5 weight percent and 7 weight percent wax oils. The DSC data were collected in the heating condition at the rate of 1° C./min. The amount of solid wax in both cases shows good match to each other in measured range. Showing that this embodiment is comparable to the DCS method in determining solid wax amount.

Figure 6:
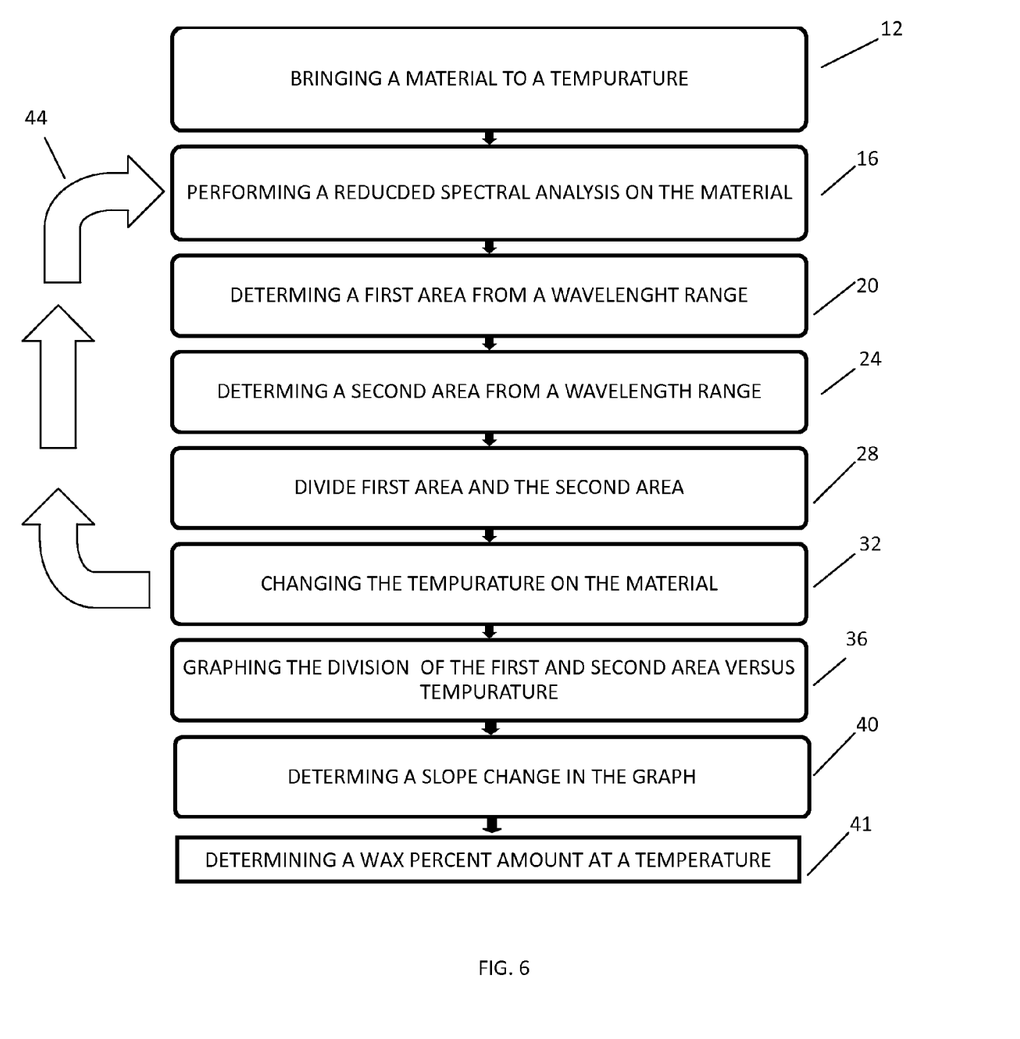
FIG. 6 is a method for determining a material property.

FIG. 6 is a method for determining a material property. In one embodiment the method includes bringing a material to a temperature 12, performing a reduced spectral analysis on the material 16, determining a first area from a wavelength range 20, determining a second area from a wavelength range 24, dividing the first area by the second area 28, changing the temperature on the material 32, repeating steps 16, 20, 24, 28, and 32 at least three times 44, creating a graph of the first and second area versus temperature 36, and determining a slope change in the graph. The method further includes determining a wax percent amount at a temperature. In one embodiment the material property is the WAT. The material in step 16 is an oil and process is repeated 11 times.

EXAMPLES

The determination of the WAT and precipitated wax amounts were performed by FTIR spectroscopy. Below are some examples.

Example 1

FIG. 3 shows the precipitated wax amount versus temperature. Two waxy oils, 5 weight percent and 7 weight percent, were examined. Differential scanning calorimeter data were added in FIG. 3 to compare the values. It should be noted that there is no measurement superiority between FTIR and differential scanning calorimeter. In terms of the WAT values, the higher values were obtained in FTIR method. However the solid wax amount showed similar trend in both cases.

Example 2

Figure 4:
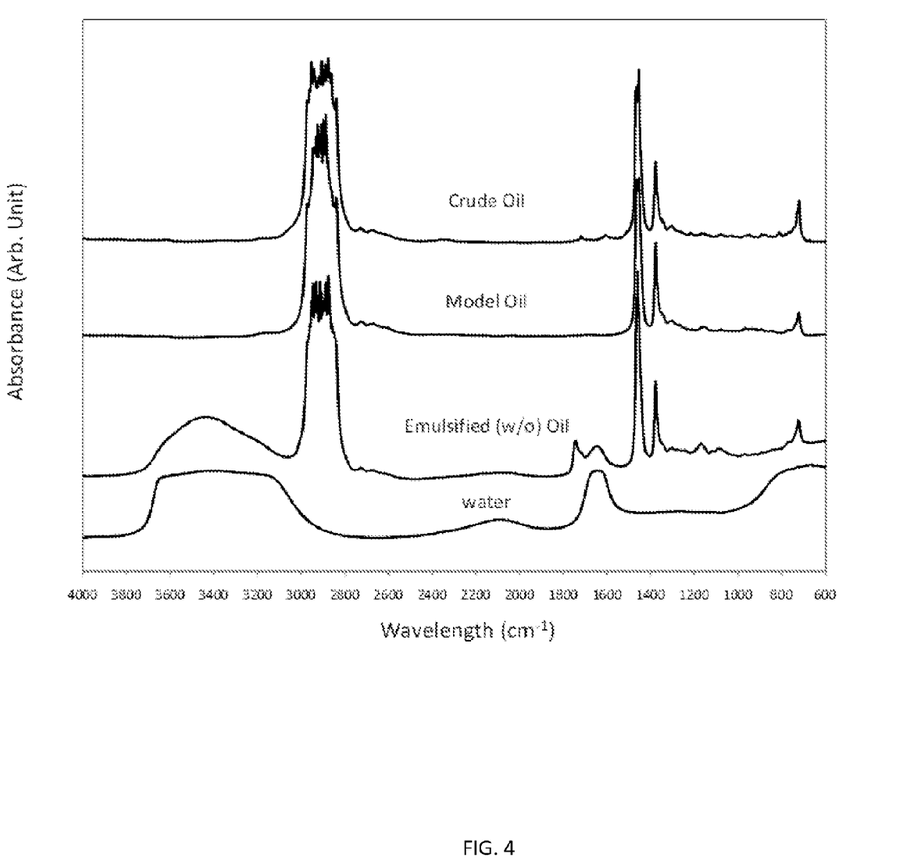
FIG. 4 is the FTIR spectra of crude oil, formulated model oil, emulsified oil and water.

FIG. 4 shows the FTIR full spectra of a crude oil, a model oil, an emulsified oil and water at the wavelength of 4000-600 $cm^{-1}$. There is no significant difference between a crude oil and the model oil. However, the spectra baseline shifted up in the presence of water that is noticeable in the emulsified oil compared to the water-free model oil. This invention expands the method applicable range even in the baseline shift up in the existence of water in oils. WAT data of anhydrous, 10 weight percent water, and 30 weight percent water emulsified oils are 22.5° C., 22.0° C., and 19.4° C., respectively. The result shows that the WAT value decreases with increasing the water amount.

Figure 5:
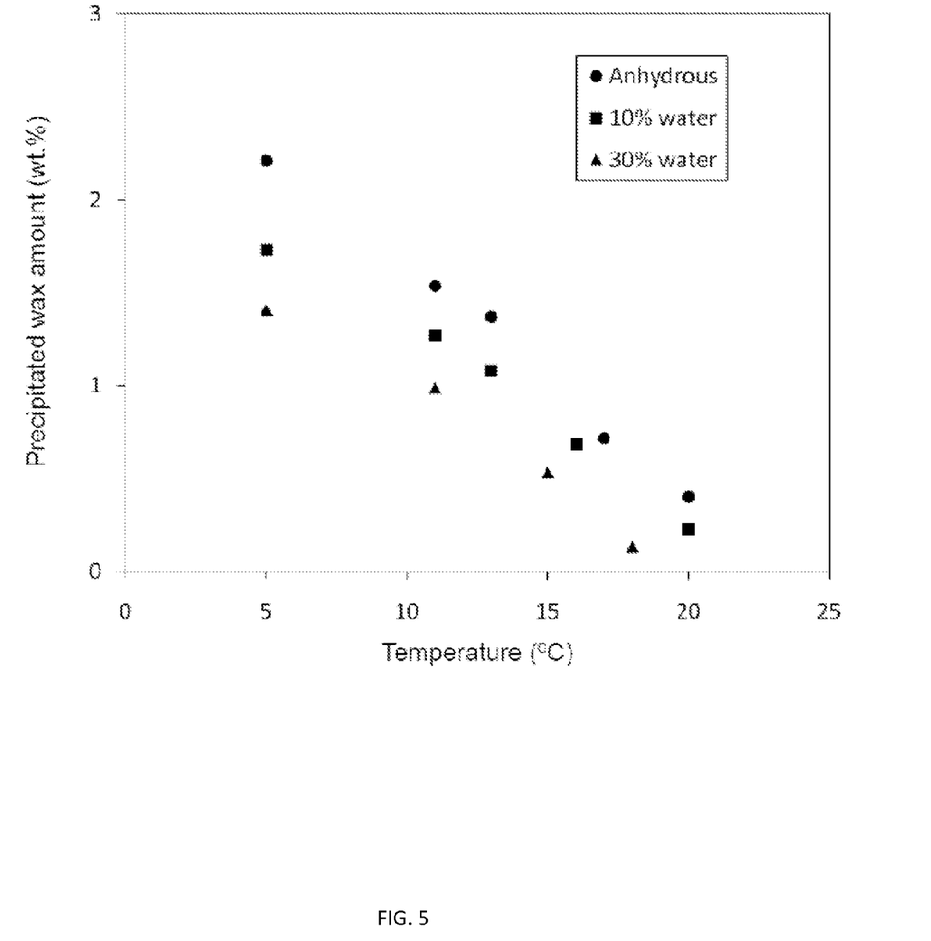
FIG. 5 is the precipitated wax amount with respect to the temperatures measured with water-in-oil emulsified oils.

FIG. 5 shows the precipitated wax amount with respect to temperatures in water-in-oil emulsified oils. All three oils showed the increase of precipitated wax contents. The smaller increase of solid wax content was observed in the higher water contents. The example provides the reliable data even in the presence of water. The invention shows the possible application to the multiphase condition. The multiphase condition means the oil is a combination of gas, liquid and/or solid material.

Example 3

Table 5 and 6 show the procedure to determine the WAT and the precipitated wax amounts in temperature variance. S1 and S2 represent the corrected area at the wavelength range of 1402-1324 $cm^{-1}$ and 735-715 $cm^{-1}$, respectively. S1 values in this temperature range do not change much. Two regressions were calculated from the mild linear increase between 60° C. and 45° C. and the data set between 40° C. and 25° C. to show the linearity. WAT value was determined to 41° C. by x-axis value of the interception between two regressions.

TABLE 5

Reduced spectral areas and regressions of waxy crude oil (18 weight percent wax content measured at 0° C.).

| Temp. (° C.) | S1 | S2 | S2/S1 | S2/S1 | S2/S1 |
|---|---|---|---|---|---|
| 60 | 25.2178 | 2.1984 | 0.087177 | | |
| 55 | 25.3572 | 2.3669 | 0.093342 | | |
| 50 | 25.4728 | 2.5868 | 0.101551 | | |
| 45 | 25.5741 | 2.7991 | 0.109451 | | |
| 40 | 25.6325 | 3.1247 | | 0.121904 | |
| 35 | 25.5900 | 3.9927 | | 0.156026 | |
| 30 | 25.5111 | 4.8578 | | 0.190419 | |
| 25 | 25.5015 | 5.7075 | | 0.223810 | |
| 20 | 25.5043 | 6.3856 | | | 0.250373 |
| 15 | 25.5462 | 6.8643 | | | 0.268701 |
| 10 | 25.5712 | 7.3555 | | | 0.287648 |
| 5 | 25.5763 | 7.7183 | | | 0.301775 |
| Regression | — | — | y = −0.00150x + 0.39411 $R^2$ = 0.99996 | y = −0.00680x + 0.17666 $R^2$ = 0.99636 | — |

TABLE 6

Calculation of precipitated wax amounts from a crude oil containing 18 weight percent wax at 0° C. Weight percent was calculated using (Eq. 16).

| Temp. (° C.) | S2/S1 | extrapolation | Difference | Wt. % |
|---|---|---|---|---|
| 60 | 0.087177 | — | — | — |
| 55 | 0.093342 | — | — | — |
| 50 | 0.101551 | — | — | — |
| 45 | 0.109451 | — | — | — |
| 40 | 0.121904 | 0.11666 | 0.005244 | 0.629260 |
| 35 | 0.156026 | 0.12416 | 0.031866 | 3.823895 |
| 30 | 0.190419 | 0.13166 | 0.058759 | 7.051089 |
| 25 | 0.223810 | 0.13916 | 0.08465 | 10.15804 |
| 20 | 0.250373 | 0.14666 | 0.103713 | 12.44562 |
| 15 | 0.268701 | 0.15416 | 0.114541 | 13.74497 |
| 10 | 0.287648 | 0.16166 | 0.125988 | 15.11854 |
| 5 | 0.301775 | 0.16916 | 0.132615 | 15.91386 |

This invention uses the universal usage of FTIR spectra to predict a WAT and a wax amount precipitated at temperatures below the WAT. Major advantages of this invention are listed below.

1) a change in the baseline does not affect to the result
2) A change in location where the FTIR light source passes through sample cell does not affect to the result 3) Significant volume changes during measurement does not affect the result 4) Sample thickness does not affect to the result 5) Moisture generation on the outer surfaces of FTIR crystal couple (NaCl) during cooling process does not affect to the result 6) The water content in the sample does not affect to the result 7) Since the invention does not require the clearness of NaCl crystals for better resolution, the reuse number of NaCl crystals can be considerably increased.

The invention can be applicable with the PTFE IR Card (purchased from the International Crystal Laboratories) whose spectra do not overlap in the wavelength ranges to determine the WAT and solid wax amount even though FTIR background shifts up.

Although the operations of the method(s) herein are shown and described in a particular order, the order of the operations of each method may be altered so that certain operations may be performed in an inverse order or so that certain operations may be performed, at least in part, concurrently with other operations. In another embodiment, instructions or sub-operations of distinct operations may be implemented in an intermittent and/or alternating manner.

Although specific embodiments of the invention have been described and illustrated, the invention is not to be limited to the specific forms or arrangements of parts so described and illustrated. The scope of the invention is to be defined by the claims appended hereto and their equivalents.

What is claimed is:

1. A method for determining a wax appearance temperature for a material comprising:
   a first process comprising;
   performing a reduced spectral analysis on the material and producing a first wavelength range at a temperature;
   determining a first area for a second wavelength range wherein the first area is defined by the area under a first peak of the reduced spectral analysis;
   determining a second area for a third wavelength range wherein the second area is defined by the area under a second peak of the reduced spectral analysis;
   dividing the first area and the second area to calculate a numerical data point;
   a second process comprising;
   repeating the first process at least three times using the material at a different temperature for each repetition and calculating a numerical data point for each process;
   creating a data representation showing the division of the first area and the second area versus the temperatures;
   determining a slope change in the data representation; and
   using the slope change to determining the wax appearance temperature for the material.

2. The method of claim 1 wherein the first wavelength range is between 1402 and 1324 $cm^{-1}$.

3. The method of claim 1 wherein the material is an oil.

4. The method of claim 3 wherein the material property determined is the wax appearance temperature.

5. The method of claim 1 further comprising determining a value based on the slope change.

6. The method of claim 1 wherein the second wavelength range is from 1402 to 1324 $cm^{-1}$.

7. The method of claim 1 further comprising:
   determining a numerical difference between related data points; and
   multiplying the difference by a constant.

8. The method of claim 1 wherein the material is gas condensate.

9. The method of claim 1 wherein the material is in multiphase flow.

10. A method for determining a wax appearance temperature and a solid wax amount in an oil comprising:
    a first process comprising;
    performing a reduced spectral analysis on the oil at a first temperature and producing a first wavelength at a range of 4000 and 400 $cm^{-1}$;
    determining a first area for a wavelength range from 1402 to 1324 $cm^{-1}$ wherein the first area is defined by the area under a first peak of the reduced spectral analysis;
    determining a second area for a wavelength range from 735 to 715 $cm^{-1}$ wherein the second area is defined by the area under a second peak of the reduced spectral analysis;
    dividing the first area and the second area to calculate a numerical data point;
    a second process comprising;
    repeating the first process at least three times with the oil at a different temperature for each repetition and calculating a numerical data point for each process;
    creating a Cartesian graph showing the division of the first area and the second area versus the temperatures wherein the graph shows a first line and a second line;
    determining a slope change in the graph where the first line and the second line intersect; and
    using the slope change to determining the wax appearance temperature for the material and the solid wax amount in the oil.

11. The method of claim 10 further comprising:
    determining a numerical difference between the first line and second line along a vertical axis; and
    multiplying the numerical difference by a constant.

12. The method of claim 10 where the oil is crude oil.

13. The method of claim 10 where the oil is shale oil.

14. The method of claim 10 where the oil is emulsified oil.

15. The method of claim 10 wherein the reduced spectral analysis uses clear NaCl crystals.

16. The method of claim 10 wherein the reduced spectral analysis uses opaque NaCl crystals.

17. The method of claim 10 further comprising the use of a PTFE IR Card to continuously collect the reduced spectral analysis data.

* * * * *

UNITED STATES PATENT AND TRADEMARK OFFICE
CERTIFICATE OF CORRECTION

| | | |
|---|---|---|
| PATENT NO. | : 8,326,548 B2 | Page 1 of 1 |
| APPLICATION NO. | : 12/785441 | |
| DATED | : December 4, 2012 | |
| INVENTOR(S) | : Kyeongseok Oh | |

It is certified that error appears in the above-identified patent and that said Letters Patent is hereby corrected as shown below:

On the Title Page, Item (75), the inventors name should appear as Kyeongseok Oh Signed and Sealed this
Twenty-ninth Day of January, 2013

David J. Kappos
*Director of the United States Patent and Trademark Office*